United States Patent [19]

Jervis et al.

[11] Patent Number: 4,563,180
[45] Date of Patent: Jan. 7, 1986

[54] HIGH FLOW CATHETER FOR INJECTING FLUIDS

[75] Inventors: James E. Jervis, Atherton; Dennis A. Caponigro, Pleasanton, both of Calif.

[73] Assignee: Raychem Corporation, Menlo Park, Calif.

[21] Appl. No.: 626,269

[22] Filed: Jun. 29, 1984

[51] Int. Cl.⁴ .................................................. A61M 25/00
[52] U.S. Cl. ........................................................ 604/280
[58] Field of Search ................ 604/272, 273, 274, 275, 604/58, 279, 280

[56] References Cited

U.S. PATENT DOCUMENTS

| | | |
|---|---|---|
| 315,023 | 4/1885 | Gray .................................. 604/275 |
| 701,587 | 6/1902 | Levy . |
| 1,388,172 | 8/1921 | Craddock . |
| 2,638,897 | 1/1951 | Poitras . |
| 2,734,665 | 11/1951 | Flamm . |
| 3,094,124 | 6/1960 | Birtwell . |
| 3,227,161 | 1/1966 | DeLorenzo ........................... 604/58 |
| 3,386,438 | 6/1968 | Stevens ............................... 604/272 |
| 3,400,714 | 5/1965 | Sheridan . |
| 3,485,234 | 4/1966 | Stevens . |
| 3,890,976 | 6/1975 | Bazell et al. . |
| 4,239,042 | 12/1980 | Asai . |
| 4,282,876 | 8/1981 | Flynn . |
| 4,335,718 | 6/1982 | Calabrese ............................ 604/272 |
| 4,385,635 | 5/1983 | Ruiz . |
| 4,405,314 | 9/1983 | Cope . |

FOREIGN PATENT DOCUMENTS

| | | | |
|---|---|---|---|
| 844642 | 7/1952 | Fed. Rep. of Germany | ...... 604/279 |
| 2427777 | 2/1975 | Fed. Rep. of Germany . | |
| 2811278 | 9/1979 | Fed. Rep. of Germany . | |
| 2119261 | 8/1972 | France . | |

Primary Examiner—John D. Yasko
Attorney, Agent, or Firm—Ira D. Blecker; Gene Dillahunty; Herbert G. Burkard

[57] ABSTRACT

There is disclosed a high flow catheter for injecting fluids into a mammalian body. The catheter has an inside diameter, a proximal end for attachment to a fluid source and a distal end for insertion into the body. The inside diameter of the catheter varies over its length from a minimum at the proximal end to a maximum at the distal end.

6 Claims, 3 Drawing Figures

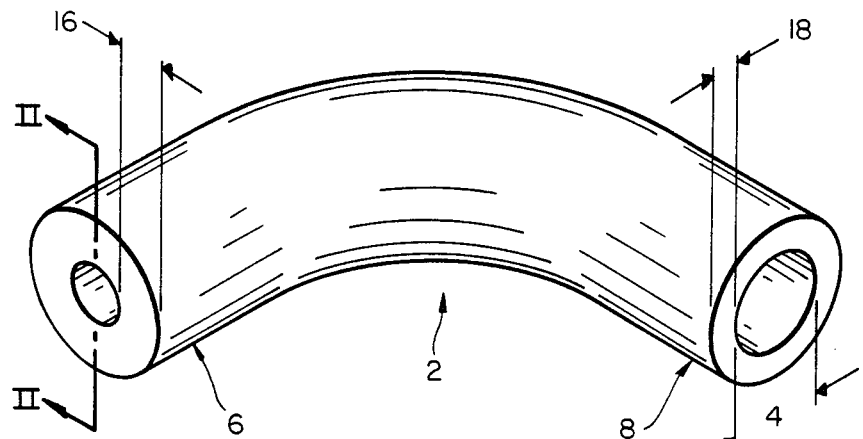
FIG_1
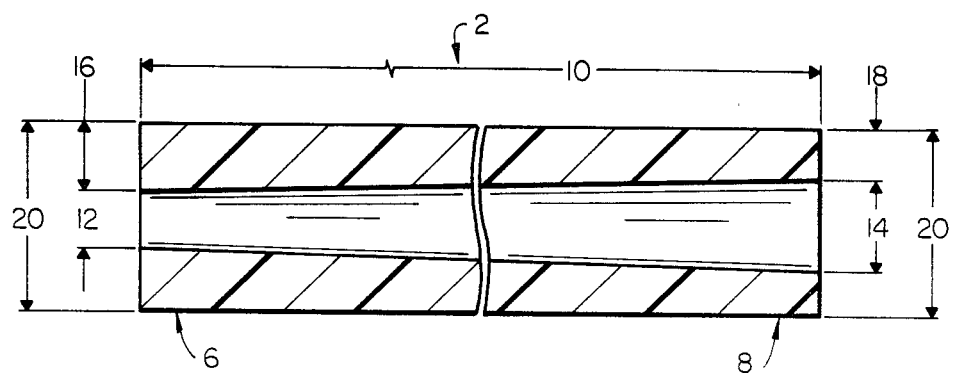
FIG_2
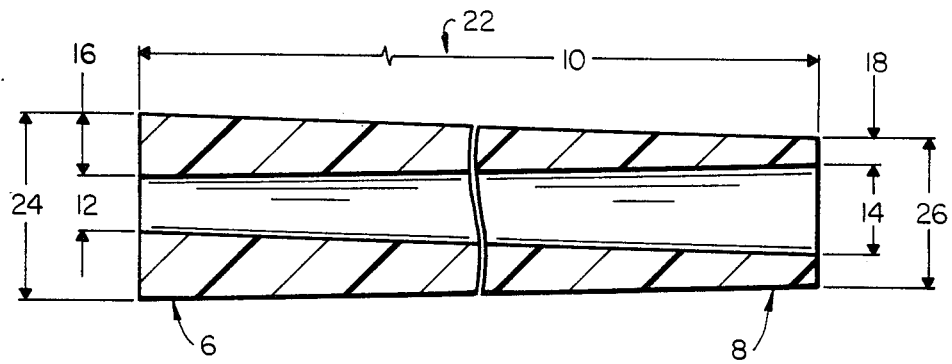
FIG_3

HIGH FLOW CATHETER FOR INJECTING FLUIDS

BACKGROUND OF THE INVENTION

This invention relates to the field of catheters and, more particularly, relates to those catheters utilized for injecting fluids into a mammalian body.

Present-day catheters generally have a main body section in which the outside and inside diameters remain the same along the whole length of this section. These catheters may have a tip portion wherein the outside and inside diameters taper at the distal end. Illustrative are Cope, U.S. Pat. No. 4,405,314 (drainage catheter); Birtwell, U.S. Pat. No. 3,094,124 (arterial catheter); and Levy, U.S. Pat. No. 701,587 (catheter). In French Patent No. 2,119,261 there are shown configurations in which the inside and outside diameters vary along the length of the catheter.

Some catheters and other medical devices have a relatively small portion at the distal end in which the inside diameter diverges. Illustrative are Bazell et al., U.S. Pat. No. 3,890,976 (catheter tip assembly); Calabrese, U.S. Pat. No. 4,335,718 (needle cannula); Sheridan, U.S. Pat. No. 3,400,7814 (nasal cannula); Fresevins German, No. 05 2811 278 (cannula); and Poitras, U.S. Pat. No. 2,638,897 (flared exit phlebotomy needle). The outside diameters of these devices at the distal end may diverge, taper, or remain constant.

In Flamm, U.S. Pat. No. 2,734,665, there is a fluid device having a nozzle wherein the inside diameter varies over the length of the nozzle from a minimum at the proximal end to a maximum at the distal end. The outside diameter may taper toward the distal end. This nozzle is relatively short when compared to the length of a catheter. There is no indication that greater flow rate can be obtained with this configuration.

When injecting fluids into a mammalian body, e.g., a human body, it is often desirable to inject the fluids as rapidly as possible. However, due to the constraints imposed by trauma or the size of the vessels, the catheters used for injecting the fluids can only be of limited diameter. Flow rate is also limited by the strength of the catheter material since the wall thickness can only be so thin, dependent of course on the material, before the catheter bursts. No attempt has been made to alter the inside diameter along the length of the catheter to increase the flow rate. Accordingly, the flow rate possible for injecting fluids is necessarily limited with present-day catheters. It thus becomes desirable to optimize the design of the catheter so as to increase the flow rate.

It does not appear that any of the above prior art suggests a catheter for injecting fluids having an inside diameter which varies over the length of the catheter from a minimum at the proximal end to a maximum at the distal end. Nor does any of the prior art suggest varying the catheter configuration so as to increase the flow rate.

Accordingly, it is an object of this invention to optimize the design of the catheter for injecting fluids.

It is another object of the invention to vary the catheter configuration so as to increase the flow rate possible.

It is a further object of the invention to have a catheter that will increase the flow rate when injecting fluids but will not increase the amount of vascular trauma.

These and other objects of the invention will become apparent from reference to the following description considered in conjunction with the accompanying figures.

BRIEF SUMMARY OF THE INVENTION

According to the invention there is disclosed a catheter for injecting fluids into a mammalian body. The catheter has an inside diameter, a proximal end for attachment to a fluid source, and a distal end for inserting into the body. The inside diameter of the catheter varies over its length from a minimum at the proximal end to a maximum at the distal end.

It has been found that such a design reflects an optimization of catheter design which results in an increase in flow rate over the prior art catheters.

BRIEF DESCRIPTION OF THE DRAWINGS

FIG. 1 is a perspective view of a catheter according to the invention.

FIG. 2 is a sectional view of the catheter of FIG. 1 in the direction of arrows II—II.

FIG. 3 is a sectional view similar to FIG. 2 of a second embodiment of a catheter according to the invention.

DETAILED DESCRIPTION OF THE INVENTION

Referring to the Figures in more detail and particularly referring to FIG. 1, there is disclosed a catheter 2 for injecting fluids into a mammalian body, for example a human body. The catheter has an inside diameter generally indicated by 4, a proximal end 6 for attachment to a fluid source (not shown), and a distal end 8 for insertion into the body (also not shown). The inside diameter of the catheter varies over its length from a minimum at the proximal end to a maximum at the distal end.

Now referring to FIG. 2, the cross section of the catheter of FIG. 1 is shown. It can be clearly seen in FIG. 2 that the inside diameter of the catheter varies over its length 10 from a minimum 12 at the proximal end 6 of the catheter to a maximum 14 at the distal end 8 of the catheter.

It can also be seen from FIGS. 1 and 2 that the catheter has a wall thickness which also varies over its length. The wall thickness varies from a maximum 16 at the proximal end of the catheter to a minimum 18 at the distal end of the catheter. In one preferred embodiment of the catheter, as shown in FIG. 2 the catheter would have a constant outside diameter 20 over substantially the entire length of the catheter.

Referring now to FIG. 3 there is shown a second embodiment of the catheter. The catheter 22 in FIG. 3 is the same as the catheter 2 of FIG. 2 except now the catheter 22 has an outside diameter which varies over its length from a maximum 24 at the proximal end 6 of the catheter to a minimum 26 at the distal end 8 of the catheter. In other respects the catheter 22 is the same as that shown in FIGS. 1 and 2, which includes the feature that the inside diameter of the catheter varies over its length from a minimum at the proximal end to a maximum at the distal end.

It is, of course, anticipated that the varying of the inside diameter of the catheter shown in FIGS. 1 to 3 can take many shapes. That is, it is not necessary that the transition from the minimum inside diameter to the maximum inside diameter occur gradually and uniformly. However, it is particularly preferred that the inside diameter tapers toward the proximal end of the catheter.

Similarly, at least with respect to the FIG. 3 embodiment, while the outside diameter of the catheter can vary over its length, it is preferred that the outside diameter vary by tapering toward the distal end.

In either of the embodiments of the catheter, it has been found that when the distal inside diameter 14 of the catheter is about 1.4 times the proximal inside diameter 12 of the catheter, certain advantageous effects of the invention will follow.

All the materials of construction commonly utilized in catheters are suitable for use with the catheter according to the invention. For purposes of illustration, and not of restricting the scope of the invention, some of these common catheter materials are polyurethane, polyethylene, polyamide, polytetrafluoroethylene, and silicone.

The instant invention is all the more significant as it runs contrary to current practice. This is true for two important reasons. The first reason is that a catheter having a varying internal diameter is difficult to manufacture. Therefore, one wishing to alter the design of the catheter would tend to avoid varying the internal diameter of the catheter and instead, choose a design that was easier to manufacture. The second reason is that when catheters are pressure-tested during manufacture they are simply clamped at one end and pressure is applied until the catheter bursts. According to this method of testing, which is inconsistent with actual use, the catheter will almost certainly fail at the thinnest wall thickness. Therefore the wall thicknesses of all catheters tend to be uniform.

Apparently it has not been recognized in the field of catheter design that further downstream from the entry of the fluid source, the pressure drastically decreases so that the thickness of the wall does not have to be as great. The following explanation may be instructive. The hydraulic forces involved in a tubular member can be approximated by the following equation:

$$PR = \sigma(t)$$

where
P = pressure
R = radius of tube
$\sigma$ = stress on the wall
t = thickness of tube If the pressure decreases downstream from the entry of the fluid source, there must also be a corresponding drop in stress on the wall of the tube. Accordingly the thickness of the wall of the tube can be decreased downstream from the entry. In other words, the thickness of the wall of any tube under pressure must be at a maximum at the entry point of the pressure and at a minimum at the discharge end of the tube.

It has been found that the most beneficial results from varying the wall thickness occur when the inside diameter is varied from a minimum at the proximal end (entry of fluid source) to a maximum at the distal end (discharge of fluid).

A standard catheter was compared with a catheter according to the invention. The standard catheter had a constant inside diameter and outside diameter. The catheter according to the invention had a constant outside diameter and a varying inside diameter. The test results are as follows:

|  | Standard Catheter | Catheter of the Invention |
|---|---|---|
| PROXIMAL END |  |  |
| Inside Diameter, inches | 0.055 | 0.055 |
| Outside Diameter, inches | 0.102 | 0.095 |
| DISTAL END |  |  |
| Inside Diameter, inches | 0.055 | 0.073 |
| Outside Diameter, inches | 0.102 | 0.095 |
| FLOW RATE, ml/min | 625.0 | 850.0 |

The catheter according to the invention starts with an outside diameter smaller than the prior art catheter but ends up with an inside diameter greater than the prior art catheter. From the above test results, it can be seen that with the catheter according to the invention there is a substantially greater flow rate than with that of the prior art catheter.

Two conclusions can be drawn from these test results. The first is that for a given flow rate requirement, a smaller outside diameter catheter may be used; hence, vascular trauma is reduced. The second is that for a given outside diameter, a greater flow rate may be achieved, other factors such as material of construction being equal.

It will be obvious to those skilled in the art having regard to this disclosure that other modifications of this inventon beyond those embodiments specifically described here may be made without departing from the spirit of the invention. Accordingly, such modifications are considered to be within the scope of the invention as limited solely by the appended claims.

We claim:

1. A catheter for injecting fluids into a mammalian body, the catheter having an inside diameter, a proximal end for attachment to a fluid source, and a distal end for insertion into the body; the inside diameter of the catheter varying over its length from a minimum at the proximal end to a maximum at the distal end, and having a wall thickness varying over its length from a maximum at the proximal end to a minimum at the distal end.

2. The catheter of claim 1 having a constant outside diameter over its length.

3. The catheter of claim 1 having an outside diameter varying over its length from a maximum at the proximal end to a minimum at the distal end.

4. The catheter of claim 1 wherein the inside diameter tapers toward the proximal end.

5. The catheter of claim 1 wherein the outside diameter tapers toward the distal end.

6. The catheter of claim 1 wherein the distal inside diameter is about 1.4 times the proximal inside diameter.

* * * * *